(12) United States Patent
Ujhelyi et al.

(10) Patent No.: US 6,804,554 B2
(45) Date of Patent: Oct. 12, 2004

(54) ARRANGEMENT AND SYSTEM FOR ENABLING PATIENT CONTROL OF ELECTRICAL THERAPIES

(75) Inventors: Michael R. Ujhelyi, Maple Grove, MN (US); Rahul Mehra, Stillwater, MN (US); Nirav V. Sheth, Coon Rapids, MN (US); Nancy Perry Pool, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 547 days.

(21) Appl. No.: 10/053,035

(22) Filed: Oct. 19, 2001

(65) Prior Publication Data

US 2003/0078621 A1 Apr. 24, 2003

(51) Int. Cl.[7] .................................................. A61N 1/30
(52) U.S. Cl. ............................... 607/6; 607/60; 607/62; 607/63
(58) Field of Search ............................. 607/5–6, 19–20, 607/32, 59, 62–63

(56) References Cited

U.S. PATENT DOCUMENTS

| | | | |
|---|---|---|---|
| 3,311,111 A | 3/1967 | Bowers | 128/422 |
| 3,805,796 A | 4/1974 | Terry, Jr. et al. | 128/419 P |
| 4,223,679 A | 9/1980 | Schulman et al. | 128/419 PT |
| 4,365,633 A | 12/1982 | Loughman et al. | |
| 4,488,554 A | 12/1984 | Nappholz et al. | |
| 5,630,834 A | 5/1997 | Bardy | 607/5 |
| 5,662,689 A | 9/1997 | Elsberry et al. | 607/5 |
| 5,792,187 A | 8/1998 | Adams | 607/5 |
| 5,817,131 A | 10/1998 | Elsberry et al. | 607/5 |
| 5,843,139 A | 12/1998 | Goedeke et al. | 607/32 |
| 5,987,356 A | 11/1999 | DeGroot | 607/5 |
| 6,021,352 A | 2/2000 | Christopherson et al. | |
| 6,167,305 A | 12/2000 | Cammilli et al. | 607/5 |
| 6,249,703 B1 | 6/2001 | Stanton et al. | |
| 6,618,617 B2 * | 9/2003 | Chen et al. | 607/5 |

* cited by examiner

Primary Examiner—Mark Bockelman
(74) Attorney, Agent, or Firm—Girma Wolde-Michael; Paul H. McDowall

(57) ABSTRACT

A patient-controlled system for temporarily disabling an electrical cardioverting therapy in order to prepare the patient psychologically and physiologically for the pain associated with electrical cardioversion therapy. In an example embodiment, the system includes a capacitive circuit capable of charging and discharging in order to apply the electrical therapy. The implanted medical device automatically causes the capacitive circuit to charge and discharge at least once within a selected period. The system includes a patient activator device that communicates with the implanted device. A disabling circuit is also included within the implanted medical device that temporarily disables the electrical therapy application in response to the patient activator device. The system further includes an alerting arrangement that alerts the patient activator device in response to the disabling circuit. An override circuit overrides the temporary disabling of the electrical therapy application in response to the patient being in a relaxed mode.

20 Claims, 2 Drawing Sheets

ARRANGEMENT AND SYSTEM FOR ENABLING PATIENT CONTROL OF ELECTRICAL THERAPIES

FIELD OF THE INVENTION

The present invention generally relates to the management of pain associated with applying electrical cardioversion therapies. In particular, the invention relates to patient preparation in advance of application of the electrical cardioversion therapy.

BACKGROUND OF THE INVENTION

Implanted medical devices are capable of detecting and treating an arrhythmia (i.e., irregular heartbeats) in a patient. In one example, the implanted medical device includes a defibrillator that applies an electrical pulse therapy to a patient's heart upon detecting fibrillation (i.e., high, irregular heartbeat), a form of arrhythmia. Cardioverters or defibrillators discharge relatively high energy electrical shocks or pulses into or across cardiac tissue to arrest a life-threatening atrial or ventricular fibrillation upon detection by the implanted medical device. Defibrillation shocks, while highly effective at arresting the fibrillation, may occur suddenly and can cause considerable patient discomfort.

The level of discomfort that a patient experiences with defibrillation shocks is affected by many psychological factors, among which are fear and anxiety of the impending shock therapy. In one instance, the patient becomes highly distressed because the patient must rush through current activities in order to find an area for treatment, and await the application of the pre-programmed shock therapy. Patients can reduce the impact of these psychological factors by taking control over the time that the shock is applied and by physiologically preparing the body in advance of the shock delivery.

The implanted device is programmed by a physician using a programming head that is electrically connected to a programming unit similar to a personal computer. The programming of the implanted device is usually limited to the physician or a trained technician. To safeguard the patient's health, the physician programs the implanted device to automatically deliver at least one electrical shock therapy in a 24-hour period. Therefore, patient control over the application time of the shock treatment is not usually available to ambulatory patients because the patient is not authorized to program his own implanted device.

Patients can also reduce the impact of psychological factors by using any one of a number of sedatives prior to the shock delivery. Although sedation therapy may be helpful in reducing shock discomfort, sedation therapy is also impractical when the patient is traveling or when the patient needs to be alert and cannot be incapacitated by the sedative for a prolonged time period.

Accordingly, patients would be able to better manage the pain associated with electrical cardioversion therapy if they had the time to psychologically and physiologically prepare in advance of the therapy. An approach that addresses the aforementioned problems, as well as other related problems, is therefore desirable.

SUMMARY OF THE INVENTION

Various embodiments of the present invention are directed to addressing the above as well as other needs in connection with enabling a patient to control the pain associated with an electrical cardioverting therapy, by allowing the patient to control the timing of the electrical therapy. In one such embodiment, an implanted medical device is configured to automatically cause the application of an electrical therapy at least once within a selected period (e.g., 24-hour period), includes a circuit arrangement for temporarily disabling the electrical therapy application responsive to a patient activated device that is carried by the patient.

According to another embodiment of the invention, a system for temporarily disabling an electrical therapy application by an implanted medical device includes a capacitive circuit capable of charging and discharging in order to apply the electrical therapy. The implanted medical device automatically causes the capacitive circuit to charge and discharge at least once within a selected period. The system includes a patient activator device that communicates with the implanted device. A disabling circuit is also included within the implanted medical device that temporarily disables the electrical therapy application in response to the patient activator device. The system further includes an alerting arrangement that alerts the patient activator device in response to the disabling circuit. The system also includes an override circuit that overrides the temporary disabling of the electrical therapy application in response to the patient being in a relaxed mode.

According to yet another embodiment of the present invention, an implanted medical device that automatically applies an electrical therapy to a patient's heart at least once within a selected period includes a communications circuit that enables telemetric communications from the implanted medical device in response to an external patient activator device. A disabling circuit is disposed within the implanted medical device that temporarily disables the electrical therapy application. An alerting arrangement is also include that alerts the patient activator device in response to the disabling circuit. The implanted medical device further includes an override circuit that overrides the temporary disabling of the electrical therapy application in response to the patient being in a relaxed mode.

The above summary of the present invention is not intended to describe each illustrated embodiment or every implementation of the present invention. The figures in the detailed description that follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
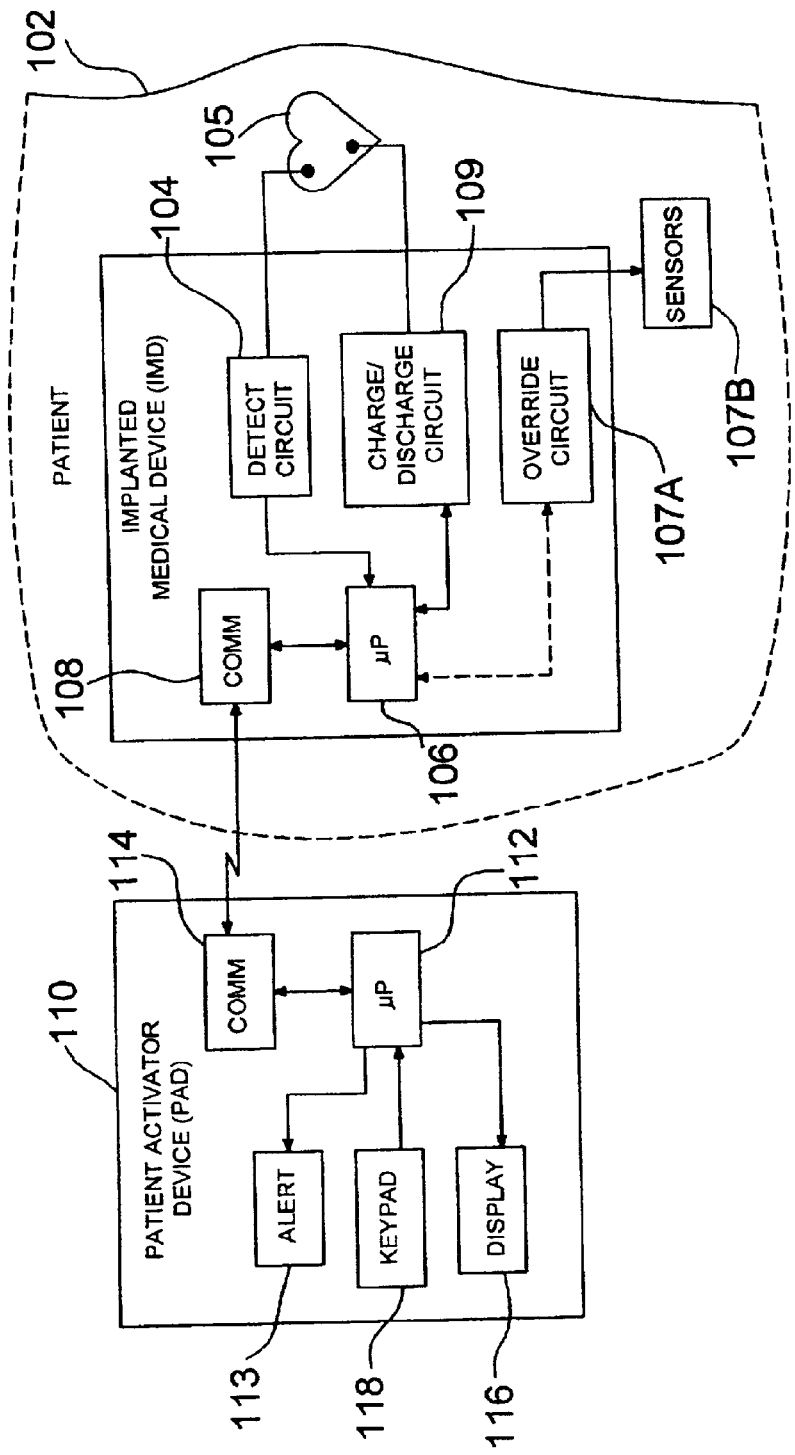
FIG. 1 illustrates a block diagram of a patient-controlled system for temporarily disabling an electrical therapy provided by an implanted device according to an example embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is generally directed to a patient-controlled system that enables a patient to control the pain associated with an electrical cardioverting therapy by controlling the time that the electrical therapy is applied. While the present invention is not necessarily limited to such an application, the invention will be better appreciated using a discussion of example embodiments in such a specific context.

In an example embodiment, a system for delivering an electrical cardioverting therapy to a heart of a patient experiencing atrial fibrillation includes an implanted medical device that delivers the electrical cardioverting therapy within a predetermined time period upon detecting the fibrillation. The implanted medical device includes a capacitive circuit that can be charged and discharged in response to a first and a second signal, respectively. The implanted device automatically transmits the signals at least once within a predetermined time period (e.g., 24-hours) causing the capacitive circuit to charge and discharge and transmits the signals in response to the detected fibrillation. The system includes a patient activator device (PAD) that is carried by the patient and that communicates an instruction to the implanted device to temporarily disable the implanted device's control over the timing of the electrical therapy. The PAD device includes an alert feature that advises the patient that the electrical therapy is temporarily disabled.

In a related embodiment, the system includes a sleep monitor that is activated by the PAD and ensures that the patient is at least relaxed or asleep when he receives the electrical therapy. In another related embodiment, the sleep monitor is automatically activated when the implanted device detects an arrhythmia. The sleep monitor is programmable by the patient via the PAD.

FIG. 1 illustrates a block diagram of a patient-controlled system 100 for temporarily disabling an electrical therapy provided by an implanted device according to an example embodiment of the invention. A patient 102 has an implanted medical device 103 that is configured to detect an abnormal body function, such as an arrhythmia (irregular heartbeat) of a heart 105. In this example, a detection circuit 104 detects an atrial fibrillation of the heart and transmits a warning signal via a communications module 108 to a patient activator device (PAD) 110. PAD 110, which can be carried, sounds an audible alarm (or emits a vibration) via an alert unit 113, in response to the warning signal from implanted device 103 alerting patient 102 that his heart is in atrial fibrillation.

Patient 102 uses PAD 110 to instruct implanted device 103 to temporarily disable the implanted device's automatic atrial fibrillation response. In this example, the automatic response is application of an electrical cardioverting therapy or shock via a charge/discharge circuit 109 to heart 105. Alert unit 113 advises the patient that the electrical therapy is temporarily disabled. System 100 also includes an override circuit in the form of a sleep monitor circuit 107A (with sensor 107B) that is activated by PAD 110 and, in conjunction with PAD 110, ensures that the patient is at least relaxed or asleep when he receives the electrical therapy.

To induce relaxation or sleep prior to the application of the electrical therapy, patient 102 can choose to take a sedative. After taking the sedative, the patient activates sleep monitor circuit 107A, which monitors the patient's physiological condition. If the patient decides not to take a sedative, the patient activates the sleep monitor when he is reclined or seated. Charge/discharge circuit 109 applies the electrical therapy to the patient upon detecting that the patient is in a relaxed mode or is asleep. In a related embodiment, a timing circuit is activated as part of the sleep monitor to ensure that the patient is asleep for a select period of time before applying the electrical therapy.

Heart conditions detectable by detection circuit 104 include, but are not limited to, ventricular fibrillation, tachycardia, bradycardia and eventual heart failure. In a related embodiment, a logic unit 106 in conjunction with detection circuit 104, evaluate the severity of the detected heart condition. Logic unit 106 continues to monitor the general condition of heart 105 before triggering detection circuit 104 to warn patient 102 of a detected arrhythmia. Implanted device 103 is also programmed to automatically deliver additional electrical therapies or shocks if a preceding shock was either ineffective or an atrial tachyarrhythmia prematurely re-occurred.

In the present embodiment, PAD 110 is comprised of a communications module 114 that communicates bi-directionally with implanted device 103 via communications module 108. PAD 110 also includes a logic unit 112 (e.g. microprocessor) that configures the electrical therapy that is applied by implanted device 103. Unit 112 also processes warning signals from implanted device 103 and transmits them to an alert unit 113 that audibly advises patient 102 of the bi-directional communication occurring between implanted device 103 and PAD 110. In this example, PAD 110 also includes a display 16 for reading alphanumeric messages from implanted device 103 and a keypad 118 for facilitating programming of implanted device 103.

In another example embodiment, implanted device 103 is an implantable cardiac defibrillator (ICD) having programmable atrial tachyarrhythmia therapies with the capability to accept programmed commands from the PAD. The ICD also includes a PAD programming capability with several automatic shock and patient activated shock therapy options. A programmable option in the ICD will allow the patient to suspend therapy for a programmable duration (e.g., one-day). ICD is also capable of delivering an electrical therapy on patient-command via PAD 110. A first signal from PAD 110 charges circuit 109 and a second signal from PAD 110 discharges circuit 109 into heart 105. The override circuit (e.g., sleep monitor circuit) of implanted device 103 is also programmable and PAD includes additional features to assist the patient to include: a query function to determine status of atrial rhythm status; immediate delivery of an electrical therapy; an atrial defibrillation deactivation button; and a programmable delay function that can suspend therapy for up to a selected period of time (e.g., 24–48 hours).

With respect to sleep monitor 107A, factors such as respiration rate, heart rate and patient activity are highly affected by sleep and are monitored by sleep monitor 107A. Once activated, monitor 107A attempts to detect a patient's state of relaxation or sleep. An example algorithm used by monitor 107A for detecting sleep requires detecting a low activity level and a 15%–25% reduction in respiration and/or heart rate (suggested physiological measures). If monitor 107A does not detect sleep within two hours, then the electrical therapy will be canceled. In another embodiment, the physiologic measures are combined with a timing circuit to ensure a steady state of sleep for a certain period of time before delivering the electrical therapy. This approach prohibits delivering the electrical therapy when the patient has just fallen asleep and is not yet entered REM sleep.

In a related embodiment, the patient is audibly warned (or via a vibration or light signal) by PAD 110 that the electrical therapy is to be administered shortly. In another related embodiment, PAD 110 has a programmable delay with a locking feature to ensure that the patient cannot alter the delay. The time delay can be based on the peak effect of the sedation therapy.

In a related embodiment, implanted device 103 comprises a neurological implant or nerve stimulator that includes a stimulator circuit. Logic unit 106 with detection circuit 104 and at least one sensor 107B coordinates the detection of irregular body functions at or near the area of the implant. Upon detecting an irregularity at the implant area, PAD 110 receives telemetric communications from implanted device 103 of the irregularity and provides an alert to the patient. The stimulator circuit delivers the electrical therapy to the area upon sensing that the patient is in a relaxed mode.

In the various embodiments described herein, PAD 110 is configured to operate in harmony with implanted device 103. For more information regarding the functionality of PAD 110 and IMD 103, reference may be made to U.S. Pat. No. 5,987,356 to De Groot, which is assigned to the assignee of the present invention and incorporated herein by reference.

In the various embodiments described herein, modules 108 and 114 are configured to telemetrically communicate with each other using various techniques, including magnetic-field coupling, reflected impedance coupling and radio-frequency (RF) coupling. For more information regarding magnetic-field coupling, reference may be made to U.S. Pat. No. 3,311,111 to Bower and U.S. Pat. No. 3,805,796 to Terry et al., which are assigned to the assignee of the present invention and incorporated herein by reference. For more information regarding reflected-impedance coupling, reference may be made to U.S. Pat. No. 4,223,679 to Schulman et al., which is assigned to the assignee of the present invention and incorporated herein by reference. For more information regarding RF coupling, reference may be made to U.S. Pat. No. 5,843,139 to Goedeke et al., which is assigned to the assignee of the present invention and incorporated herein by reference.

Figure 2:
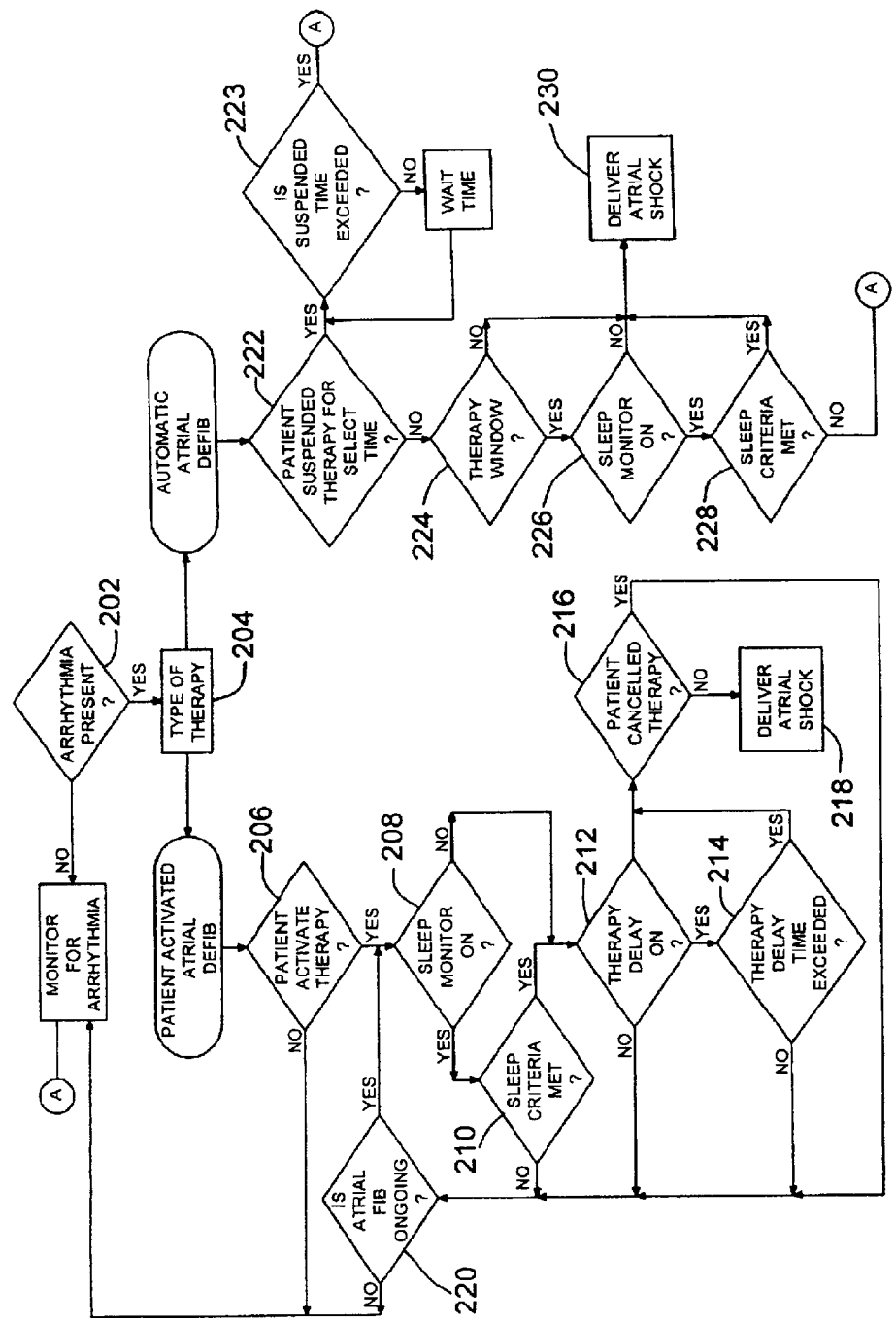
FIG. 2 is a flow diagram illustrating the manner of using a patient activator device to control the time that an electrical therapy is applied according to another example embodiment of the invention.

FIG. 2 is a flow diagram 200 that illustrates the logic in the use of a patient activator device to control the time that an electrical therapy is applied according to another example embodiment of the invention. At step 202, implanted device 103 detects the presence of arrhythmia, which in this case is atrial fibrillation. At step 204, implanted device 103 determines the type of therapeutic mode: automatic atrial defibrillation or patient-activated atrial defibrillation. At step 206 of the patient activated atrial fibrillation path, implanted device 103 determines if the patient activated the therapy via a delay timer or sleep monitor 107A. If the sleep monitor is activated at step 208, the sleep monitor determines at step 210 if the sleep criterion for the patient is met. At step 212, if the sleep criterion is met implanted device 103 determines whether a delay entered on PAD 110 is still engaged. If the therapy delivery time is exceeded in step 214, then implanted device 103 determines whether the patient canceled the therapy. At step 218, the implanted device applies the electrical therapy because the therapy was not actually canceled.

At step 206, implanted device 103 determines that the patient did not activate a therapy, and device 103 continues to monitor for ongoing AF (atrial fibrillation) at step 220. At step 208, if implanted device 103 determines that the sleep monitor is not on then implanted device 103 verifies whether a delay is engaged. If no delay is detected, then at step 216, implanted device 103 determines that the therapy was indeed canceled and continues to monitor for ongoing AF. Device 103 also continues to monitor for AF when the implanted device determines that at step 214 the therapy time delay has been exceeded. At step 210, implanted device 103 determines that the sleep criterion is not met and continues to monitor for ongoing AF.

At step 222 on the automatic atrial defibrillation path, device 103 determines whether the patient has suspended the atrial defibrillation therapy for a fixed time period. If at step 223, implanted device 103 determines that the suspended time is exceeded then device 103 continues to monitor for AF. At step 224, implanted device 103 determines if there is a pre-programmed window for therapy (e.g., 4AM–6AM, daily). If there is no therapy pre-scheduled, at step 226 device 103 determines whether the sleep monitor is on. If at step 228, device 103 determines that the sleep monitor is on and the sleep criteria is met device 103 delivers the shock therapy to heart 105 at step 230.

Device 103 delivers a shock to the heart at step 224 if there is no therapy window and at step 226 if sleep monitor circuit 107A is not on. Device 103 will continue to monitor for ongoing AF whenever device 103 determines that the sleep criterion is not met.

Various modifications, equivalent processes, as well as numerous applications to which the present invention may be amenable will be readily apparent to those of skill in the art to which the present invention is directed, upon review of the present specification. The claims are intended to cover such modifications and devices.

We claim:

1. A system for temporarily disabling an electrical therapy application by an implanted medical device, the implanted medical device including a capacitive circuit adapted to charge and to discharge such that the electrical therapy is applied, the implanted medical device automatically causing the capacitive circuit to charge and discharge at least once within a selected period, the system comprising:

a patient activator device adapted to communicate with the implanted medical device;

a disabling circuit within the implanted medical device and adapted to temporarily disable the application of the electrical therapy in response to the patient activator device;

an alerting arrangement adapted to alert the patient activator device in response to the disabling circuit; and an override circuit adapted to override the temporary disabling of the electrical therapy application in response to the patient being in a relaxed mode.

2. The system of claim 1, wherein the override circuit is adapted to enable the electrical therapy application at a selected time after the patient is in the relaxed mode, the selected time being provided by the patient activator device.

3. The system of claim 2, wherein the override circuit comprises a sleep monitoring circuit adapted to detect when the patient is in a sleep mode.

4. The system of claim 3, wherein the sleep monitoring circuit is adapted to be programmed by the patient activator device.

5. The system of claim 1, wherein the capacitive circuit is adapted to charge in response to a first signal from the patient activator device and to discharge in response to a second signal from the patient activator device such that the electrical therapy is applied.

6. The system of claim 1, wherein the override circuit is adapted to be automatically activated upon the implanted medical device detecting an arrhythmia.

7. The system of claim 1, wherein the override circuit is adapted to be activated by the patient activator device.

8. The system of claim 1, wherein the implanted medical device is an implantable cardiac defibrillator device.

9. The system of claim 1, wherein the capacitive circuit comprises a stimulator circuit adapted to deliver an electrical therapy to a selected portion of a patient's body.

10. The system of claim 9, wherein the implanted medical device is a neurological implant.

11. The system of claim 1, wherein the override circuit is adapted to use at least one physiological measure to indicate that the patient is in the relaxed mode.

12. The system of claim 3, wherein the sleep monitoring circuit is adapted to be automatically activated upon the implanted medical device detecting an arrhythmia.

13. The system of claim 1, wherein the patient activator device is adapted to enable at least one of a plurality of electrical therapy options to be applied when the patient is in the relaxed mode.

14. An implanted medical device adapted to automatically apply an electrical therapy to a patient's heart at least once in a selected time period, the implanted medical device comprising:
- a communications circuit adapted to communicate telemetrically from the implanted medical device in response to an external patient activator device;
- a disabling circuit adapted to temporarily disable the electrical therapy application;
- an alerting arrangement adapted to alert the patient activator device in response to the disabling circuit; and
- an override circuit adapted to override the temporary disabling of the electrical therapy application in response to the patient being in a relaxed mode.

15. The implanted device of claim 14, wherein the override circuit is adapted to be activated by the patient activator device and enable the electrical therapy application at a selected time after the patient is in the relaxed mode, wherein the selected time is provided by the patient activator device.

16. The implanted device of claim 14, further comprising a capacitive circuit adapted to charge in response to a first signal from the patient activator device and to discharge in response to a second signal from the patient activator device such that the electrical therapy is applied.

17. The implanted device of claim 14, wherein the override circuit is adapted to use at least one physiological measure to indicate that the patient is in the relaxed mode.

18. The implanted device of claim 14, wherein the implanted medical device is adapted to apply at least one of plurality of electrical therapy options when the patient is in the relaxed mode in response to the patient activator device.

19. A system for temporarily disabling an electrical therapy application by an implanted medical device, the implanted medical device including a capacitive circuit adapted to charge and to discharge such that the electrical therapy is applied, the implanted medical device automatically causing the capacitive circuit to charge and discharge at least once within a selected period, the system comprising:
- a patient activator device adapted to communicate with the implanted medical device;
- means, within the implanted medical device and responsive to the patient activator device, for temporarily disabling the electrical therapy application;
- means, responsive to the disabling means, for alerting the patient activator device; and
- means, responsive to the patient being in a relaxed mode, for overriding the temporary disabling of the electrical therapy application.

20. The system of claim 19, further comprising means, responsive to the patient activator device, for enabling at least one of a plurality of electrical therapy options to be applied when the patient is in the relaxed mode.

* * * * *